United States Patent
Persson et al.

(10) Patent No.: US 9,795,791 B2
(45) Date of Patent: Oct. 24, 2017

(54) SYSTEMS AND METHODS FOR DELIVERING TEST AND BACKUP PULSES FROM A SINGLE CAPACITOR

(71) Applicant: PACESETTER, INC., Sunnyvale, CA (US)

(72) Inventors: Benjamin T. Persson, Sunnyvale, CA (US); Matthew G. Fishler, Santa Cruz, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 103 days.

(21) Appl. No.: 14/878,892

(22) Filed: Oct. 8, 2015

(65) Prior Publication Data

US 2017/0100595 A1 Apr. 13, 2017

(51) Int. Cl.
*A61N 1/362* (2006.01)
*A61N 1/37* (2006.01)
*A61N 1/05* (2006.01)
*A61N 1/375* (2006.01)

(52) U.S. Cl.
CPC ........... *A61N 1/371* (2013.01); *A61N 1/0573* (2013.01); *A61N 1/3756* (2013.01)

(58) Field of Classification Search
CPC ................ A61N 1/371–1/3718; A61N 1/3756
See application file for complete search history.

(56) References Cited

U.S. PATENT DOCUMENTS

| | | | |
|---|---|---|---|
| 5,411,533 A * | 5/1995 | Dubreuil | A61N 1/3712 607/28 |
| 5,431,692 A * | 7/1995 | Hansen | A61N 1/3706 607/27 |
| 5,480,414 A | 1/1996 | Stroebel et al. | |
| 2013/0116741 A1* | 5/2013 | Bornzin | A61N 1/3756 607/9 |
| 2015/0238768 A1* | 8/2015 | Bornzin | A61N 1/37205 607/28 |

* cited by examiner

*Primary Examiner* — George Evanisko
(74) *Attorney, Agent, or Firm* — Theresa Raymer

(57) ABSTRACT

The present disclosure provides systems and methods for cardiac stimulation. A cardiac stimulation device includes a plurality of electrodes, and a pulse circuit electrically coupled to the plurality of electrodes, the pulse circuit including a capacitor configured to charge to an initial charge level, deliver a test pulse having a first amplitude to the plurality of electrodes by only partially discharging, and subsequently deliver a backup pulse to the plurality of electrodes, the backup pulse having a second amplitude that is larger than the first amplitude.

20 Claims, 4 Drawing Sheets

SYSTEMS AND METHODS FOR DELIVERING TEST AND BACKUP PULSES FROM A SINGLE CAPACITOR

FIELD OF THE DISCLOSURE

The present disclosure relates generally to cardiac stimulation systems, and more particularly to delivering test and backup pulses for threshold capture using a single output capacitor.

BACKGROUND ART

Implantable pacemakers generate electrical stimulation pulses and deliver such stimulation pulses to atrial and/or ventricular muscle tissue of a patient's heart at a prescribed rate and/or rhythm when, through disease or other cause, the heart is not able to maintain the prescribed heart rate or rhythm on its own. When the delivered electrical stimuli are of sufficient energy, they cause the cardiac muscle tissue to depolarize, and therefore contract, thereby forcing the heart rate or rhythm to track the delivery of the electrical stimuli. When the delivered electrical stimuli are of insufficient energy, depolarization does not occur, and the heart rate or rhythm is not controlled by the pacemaker. Hence, for the pacemaker to perform its intended function, it is important that the delivered electrical stimulus is of sufficient energy to depolarize the cardiac tissue.

The depolarization and ensuing contraction of the heart in response to a delivered cardiac stimulation pulse is generally referred to in the art as "capture". Consequently, the term "non-capture" denotes the condition when a delivered stimulation pulse does not result in depolarization and contraction. When detecting capture, sensing circuitry checks for the depolarization of a cardiac chamber following and in response to a delivered stimulation pulse. Such a depolarization as a result of a delivered stimulation pulse is also referred to as an "evoked response" (ER) of that chamber. Furthermore, the evoked response is detected during a selected time period following the delivery of a stimulation pulse. Such a time period is generally referred to as an "evoked response window".

The amount of energy needed to effectuate capture is known as the capture "threshold", and electrical stimuli of energy less than the capture threshold do not bring about capture, while electrical stimuli of energy greater than the capture threshold do bring about capture. A capture threshold search normally begins at a desired starting point (either a high energy level or the level at which capture is currently occurring) and the energy level is decreased until capture is lost. The smallest value at which capture is maintained is known as the capture threshold. Thereafter, in order to secure capture, a safety margin is added to the capture threshold to arrive at the energy content of the stimulation pulse.

At least some existing approaches for capture management threshold testing rely on the availability and use of two separate pacing output capacitors and associated charging circuitry. In general, a first output capacitor provides a primary pacing stimulus at a "test" amplitude and duration, and a second output capacitor provides a secondary pacing stimulus at a "backup" amplitude and duration. The backup pulse is generally delivered between approximately 50 milliseconds (ms) and 250 ms after the test pulse.

This two-capacitor approach is commonly employed because the relatively short interval between the test and backup pulses makes it essentially impractical to recharge a single tank capacitor from a test voltage level (which is generally relatively low) to a backup voltage level (which is generally relatively high) within the required timeframe.

BRIEF SUMMARY OF THE DISCLOSURE

In one embodiment, the present disclosure is directed to a cardiac stimulation device. The cardiac stimulation device includes a plurality of electrodes, and a pulse circuit electrically coupled to the plurality of electrodes, the pulse circuit including a capacitor configured to charge to an initial charge level, deliver a test pulse having a first amplitude to the plurality of electrodes, and subsequently deliver a backup pulse to the plurality of electrodes, the backup pulse having a second amplitude that is larger than the first amplitude.

In another embodiment, the present disclosure is directed to a pulse circuit for use in a cardiac stimulation device. The pulse circuit is configured to electrically couple to a plurality of electrodes and includes a capacitor, and charging/discharging circuitry electrically coupled to the capacitor and configured to charge the capacitor to an initial charge level, partially discharge the capacitor to deliver a test pulse having a first amplitude to the plurality of electrodes, and further discharge the capacitor to deliver a backup pulse to the plurality of electrodes, the backup pulse having a second amplitude that is larger than the first amplitude.

In another embodiment, the present disclosure is directed to a method to facilitate determining a capture threshold for a cardiac stimulation device. The method includes charging a capacitor to an initial charge level, only partially discharging the capacitor to deliver a test pulse having a first amplitude to a plurality of electrodes coupled to the capacitor, and further discharging the capacitor to deliver a backup pulse to the plurality of electrodes, the backup pulse having a second amplitude that is larger than the first amplitude.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for delivering both test and backup pacing pulses using a single capacitor. The capacitor is initially charged, partially discharged to deliver the test pulse, and then further discharged to deliver the backup pulse.

The systems and methods described herein may be utilized for short term use (e.g., during relatively infrequent capture management threshold test periods) or during normal operation (e.g., to provide a higher-voltage backup pace pulse after a subthreshold primary pace pulse). Performing threshold testing using a single capacitor enables capture management methods that require less external components and associated circuitry. Such simplification is particularly important in space-restricted and power-restricted systems, such as leadless pacemaker systems.

Figure 1A:
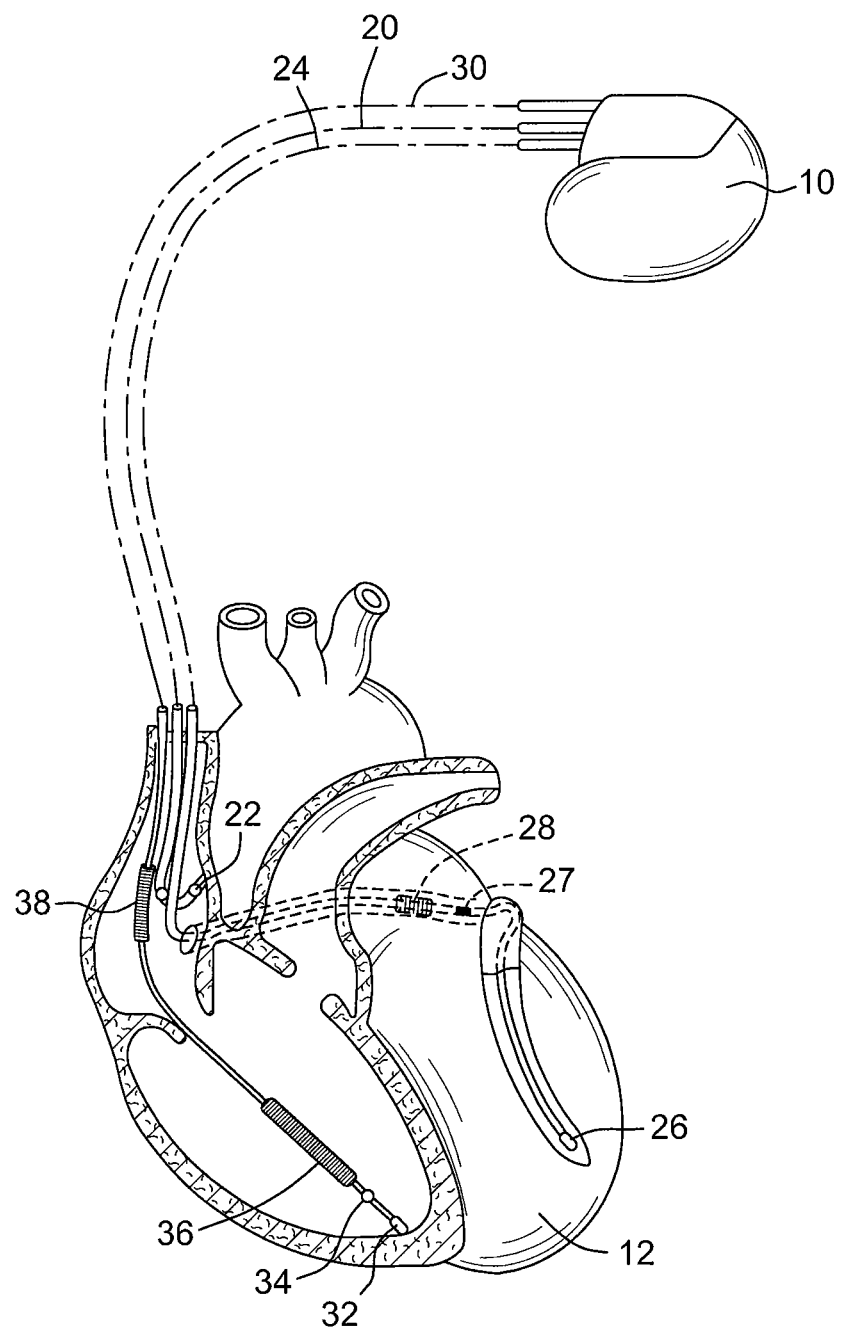
FIG. 1A is a simplified, partly cutaway view illustrating an implantable stimulation device in electrical communication with at least three leads implanted into a patient's heart for delivering multi-chamber stimulation and shock therapy, in accordance with certain embodiments herein.

FIG. 1A illustrates a stimulation device 10 in electrical communication with a patient's heart 12 by way of three leads 20, 24 and 30 suitable for delivering multi-chamber stimulation (and shock therapy). In order to sense atrial cardiac signals and to provide right atrial chamber stimulation therapy, stimulation device 10 is coupled to an implantable right atrial lead 20 having at least an atrial tip electrode 22, which typically is implanted in the patient's right atrial appendage.

In order to sense left atrial and ventricular cardiac signals and to provide left-chamber pacing therapy, stimulation device 10 is coupled to a coronary sinus lead 24 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left lateral vein, left posterior ventricular vein, middle cardiac vein, and/or small cardiac vein or any other cardiac vein accessible by the coronary sinus.

Accordingly, coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. Stimulation device 10 is also shown in electrical communication with the heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Right ventricular lead 30 may be transvenously inserted into heart 12 so as to the right ventricular tip electrode 32 in the right ventricular apex so that RV coil electrode 36 will be positioned in the right ventricle and SVC coil electrode 38 will be positioned in the superior versa cava. Accordingly, the right ventricular lead 30 is capable of receiving cardiac signals, and delivering stimulation in the form of pacing and shock therapy to the right ventricle.

Figure 1B:
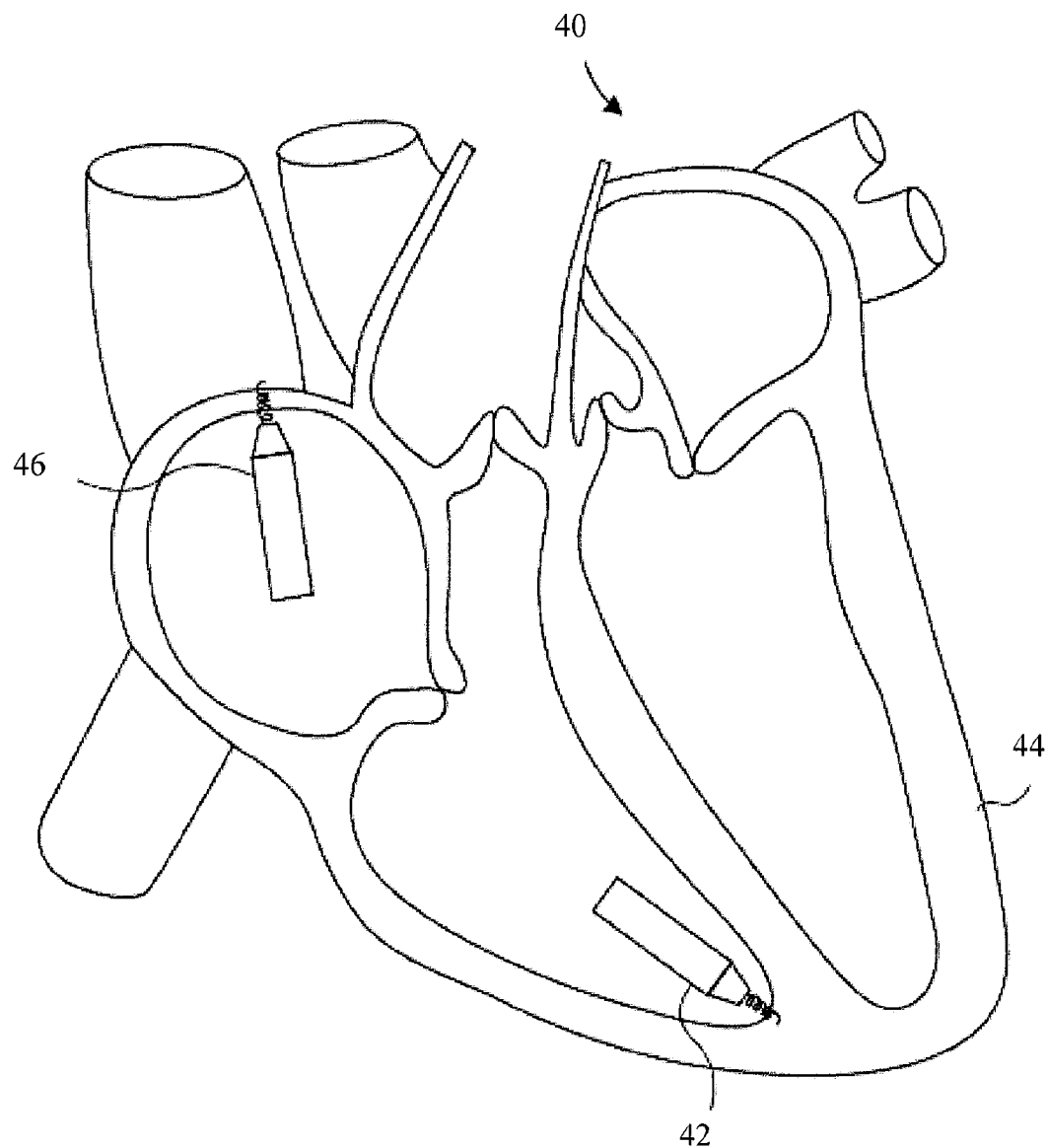
FIG. 1B is a pictorial diagram showing an embodiment of a cardiac pacing system that includes a leadless cardiac pacemaker, in accordance with certain embodiments herein.

FIG. 1B illustrates an example of leadless cardiac pacemakers 42 and 46 attached to the cardiac wall 44 of the heart 40. U.S. Pat. No. 9,126,032, issued on Sep. 18, 2015, entitled Pacemaker Retrieval Systems and Methods, and U.S. Publication No. 2012/0158111, entitled Leadless Pacemaker with Radial Fixation Mechanism, filed on Dec. 20, 2011, disclose leadless cardiac pacemakers and methods for implanting and removing leadless pacemakers, both are incorporated by reference herein in their entirety.

Notably, the systems and methods described herein may be used with any cardiac simulation device, and are not limited to stimulation devices 10, 42, and 46.

Figure 2:
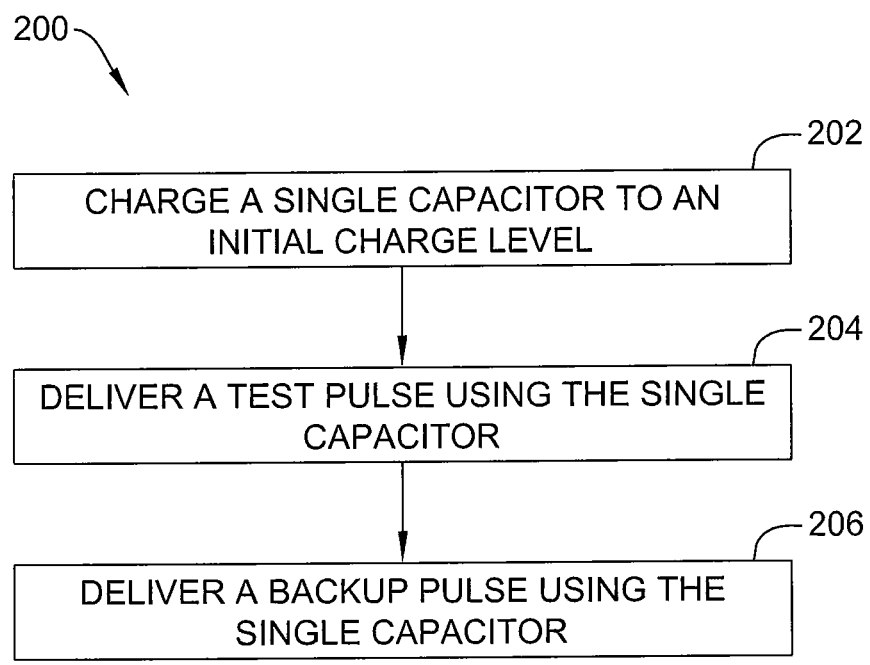
FIG. 2 is a flowchart of one embodiment of a capture method that may be used with the stimulation device shown in FIGS. 1A and 1B.

FIG. 2 is a flowchart of an example capture method 200. Capture method 200 delivers a test, or primary, pulse and a secondary, or backup, pulse in relatively rapid succession (e.g., during a single cardiac cycle) from a single capacitor, without requiring the capacitor to be recharged between the test pulse and the backup pulse. In method 200, it is assumed that an amplitude of the test pulse is less than an amplitude of the backup pulse.

At block 202, a single capacitor is charged to an initial charge level. The initial charge level is at least a backup pulse level, or amplitude. The initial charge level may be a backup pulse level plus a test pulse level. At block 204, a test pulse is delivered using the single capacitor. In this embodiment, the test pulse is delivered by regulation of the output from the single capacitor. For example a low-dropout (LDO) linear regulator may be used to provide relatively fast and accurate voltage tracking. The regulator may be programmable such that it can be controlled by a digital to analog converter (discussed below) to set an initial pulse amplitude. In another embodiment, the backup pulse could also be delivered by the LDO at a higher programmed setting.

In this embodiment, after the test pulse is delivered, at block 206 a backup pulse may be delivered using the single capacitor. As explained above, the test pulse has a low, relatively small amplitude (e.g., 0.125V to 5V, or more preferably 0.25V to 3V, or even more preferably 0.25V to 2.5V) relative to the backup pulse (e.g., 5-10V, or preferably 5V to 7.5V, and even more preferably 5V to 6V). Accordingly, even though the test pulse has already been delivered, the single capacitor still has sufficient charge to deliver the backup pulse at an amplitude that is approximately equal to initial charge level, without recharging the capacitor. The backup pulse is delivered via direct output from the single capacitor, or alternatively, via a secondary amplitude control level of the LDO, as described above. The backup pulse may be delivered after each test pulse, or may only be delivered when the test pulse is detected to be subthreshold (e.g., via evoked response testing). In certain embodiments, the backup pulse is delivered between approximately 50 milliseconds (ms) and approximately 250 ms after the test pulse.

Figure 3:
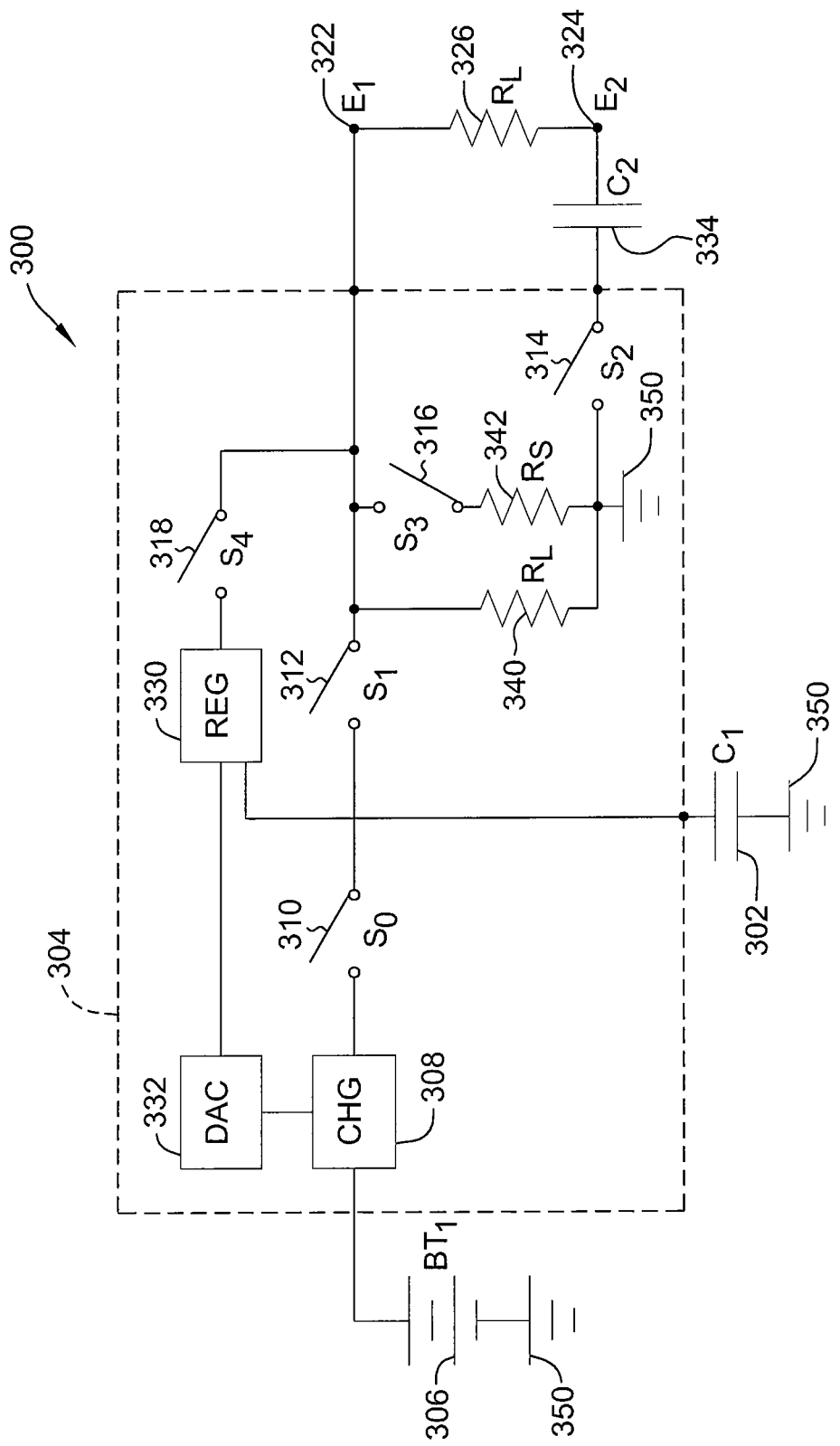
FIG. 3 is a circuit diagram of one embodiment of a pulse circuit that may be used to perform the capture method shown in FIG. 2.

FIG. 3 is a circuit diagram of one embodiment of a pulse circuit 300 for delivering a low amplitude test pulse and a high amplitude backup pulse using a single capacitor 302. In this embodiment, the backup pulse may be delivered soon after the test pulse (e.g., during a single cardiac cycle and/or between approximately 50 ms and approximately 250 ms after the test pulse). In other embodiments, the delivery of the backup pulse may be deferred to a subsequent cardiac cycle.

As shown in FIG. 3, pulse circuit 300 includes charging/discharging circuitry 304 that charges and discharges single capacitor 302. In this embodiment, a battery 306 provides power to a charging block 308. Charging block 308 charges single capacitor 302 to an initial charge level that is set by a digital to analog converter block 332 coupled to charging block 308 (e.g., corresponding to a level that will satisfy the amplitude and energy requirements both of the low amplitude test pulse and of the high amplitude backup pulse). During charging, a first switch 310 coupled between charging block 308 and single capacitor 302 is closed. In this embodiment, a second switch 312, third switch 314, fourth switch 316, and fifth switch 318 are open during charging.

Pulse circuit 300 includes a first electrode 322 and a second electrode 324 electrically coupled to charging/discharging circuitry 304. The resistance between first and second electrodes 322 and 324, mostly due to patient tissue and blood, is represented as an effective resistor 326.

To deliver the test pulse, first switch 310 is opened, and a regulator block 330 is connected to first electrode 322 by closing fifth switch 318. Regulator block 330 delivers the test pulse at a predetermined voltage that is set by a digital to analog converter block 332 coupled to regulator block 330. Alternatively, the test pulse may be shaped to emulate a capacitive discharge voltage profile (or any other desired voltage profile) via an appropriate time-series of amplitude signals from digital to analog converter block 332 to the coupled regulator block 330. For both the test pulse and the subsequently delivered backup pulse, third switch 314 is closed to connect a pace coupling capacitor 334 and to complete the circuit through effective resistor 326. In an alternative embodiment, pace coupling capacitor 334 is coupled between first electrode 322 and fifth switch 318.

As shown in FIG. 3, charging/discharging circuitry 304 further includes a first internal resistor 340 coupled between third switch 314 and fifth switch 318, and a second internal resistor 342 coupled between third switch 314 and fourth switch 316. Further, battery 306, single capacitor 302, and first and second internal resistors 340 and 342 are coupled to ground 350. After the test pulse is delivered, fifth switch 318 is opened, and fourth switch 316 is closed to quickly discharge the voltage accumulated on pace coupling capacitor 334 through second internal resistor 342. In some embodiments, discharge of pace coupling capacitor 334 through second internal resistor 342 may be postponed until after the delivery of the backup pulse (or until after it is determined that the backup pulse is not required). In this embodiment, after the discharge, third switch 314 and fourth switch 316 are re-opened to stop discharge and allow evoked response sensing.

To deliver the backup pulse (after the test pulse is detected to be subthreshold or after a predetermined delay), second switch 312 and third switch 314 are closed, and the backup pulse is delivered directly from single capacitor 302. Single capacitor 302 is discharged for a predetermined period of time (e.g., 1.5 ms) to deliver the backup pulse.

In some embodiments, single capacitor 302 may be slightly recharged between delivery of the test pulse and the backup pulse. For example, single capacitor 302 may be initially charged by analog converter block 332 to satisfy only the energy requirements of the high amplitude backup pulse, or approximately only the energy requirements of the high amplitude backup pulse, and analog converter block 332 may recharge single capacitor 302 to again satisfy the energy requirements of the high amplitude backup pulse, or approximately satisfy the energy requirements of the high amplitude backup pulse, after single capacitor 302 is discharged to deliver the test pulse. Single capacitor 302 may be recharged between delivery of the test pulse and the backup pulse by approximately the charge delivered by the test pulse.

In a specific example, single capacitor 302 may be initially charged to deliver a backup pulse having an amplitude of 5V. A test pulse having an amplitude of 0.25V will partially discharge single capacitor 302. The single capacitor 302 can then be recharged by approximately the charge delivered by the test pulse, to again have sufficient charge to deliver a backup pulse having an amplitude of 5V. Those of skill in the art will appreciate and understand that other test and backup pulse amplitudes may be used.

In some embodiments, single capacitor 302 may be initially charged by analog converter block 332 to satisfy only the energy requirements of the high amplitude backup pulse, or approximately only the energy requirements of the high amplitude backup pulse, and analog converter block 332 may recharge single capacitor 302 between a test pulse and backup pulse to voltage that is less than the energy requirements of the high amplitude backup pulse. In these embodiments, single capacitor 302 is recharged as much as possible to again satisfy the energy requirements of the high amplitude backup pulse, until a time at which pulse circuit 300 determines that a backup pulse is required. Although single capacitor 302 may not be fully recharged between delivery of the test pulse and the backup pulse, single capacitor 302 may nevertheless have sufficient charge to capture the heart.

In a specific example, single capacitor 302 may be initially charged to deliver a backup pulse having an amplitude of 5V. A test pulse having an amplitude of 0.25V will partially discharge single capacitor 302. Single capacitor 302 can then be recharged as much as possible towards the charge required to deliver a backup pulse having an amplitude of 5V before the pulse circuit 300 determines that a backup pulse is required. When the pulse circuit 300 determines that a backup pulse is required, single capacitor 302 will be discharged whether or not full recharge has been achieved, i.e., when single capacitor 302 is charged to deliver a backup pulse having an amplitude of less than 5V. Those of skill in the art will appreciate and understand that other test and backup pulse amplitudes may be used.

Alternatively, single capacitor 302 may be initially charged to a slightly higher level (e.g., to satisfy the amplitude and energy requirements both of the low amplitude test pulse and the high amplitude backup pulse). For example, single capacitor 302 may be initially charged to deliver a pulse having an amplitude of approximately 5.25V. A test pulse having an amplitude of approximately 0.25V will partially discharge single capacitor 302 towards a charge sufficient to deliver a backup pulse having an amplitude of approximately 5V. A backup pulse having an amplitude of approximately 5V will then discharge single capacitor 302, without requiring single capacitor 302 to be recharged between the test pulse and backup pulse. Those of skill in the art will appreciate and understand that other test and backup pulse amplitudes may be used.

Digital to analog converter block 332 is one example for setting a programmable reference for a regulator. Those of skill in the art will appreciate that other methods for setting the programmable reference may be used. Further, the regulator does not necessarily need to track the set voltage throughout the pulse. For example, the regulator could set the initial amplitude, and then maintain either a constant drop or constant resistance for the remainder of the pulse. This more closely matches the typical pulse discharge profile of a pacing pulse, and could be accomplished, for example, by breaking a feedback loop used for such regulators at a point during delivery of the test pulse, such that the regulation is only controlled initially.

Operation of pulse circuit 300 may be controlled by a suitable control device, such as a microcontroller. Further, pulse circuit 300, including charging block 308, regulator block 330, and digital to analog converter block 332 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

Method 200 and pulse circuit 300 may be used when determining a capture threshold, as described above. Further, method 200 and pulse circuit 300 may also be used during normal operation to ensure capture. In some embodiments, for power optimization purposes, any necessary backup pulse is delivered on a subsequent pacing cycle (as opposed to the same pacing cycle as the previously delivered test pulse). Moreover, during normal operation, regulator block 330 may be deactivated, such that digital to analog converter block 332 charges single capacitor 302 to the predetermined voltage. This also facilitates reducing a leakage current on single capacitor 302, because the average voltage will be lower.

The systems and methods described herein facilitate delivering test and backup pulses using a single capacitor. The capacitor is initially charged, partially discharged to deliver the test pulse, and then further discharged to deliver the backup pulse. Using a single capacitor for both pulses facilitates reducing both the cost and complexity of such systems.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A leadless pacemaker configured to be implanted in a patient's heart and used for selectively delivering test pacing pulses having a first amplitude and backup pacing pulses having a second amplitude that is greater than the first amplitude, the leadless pacemaker comprising:
    a plurality of electrodes; and
    a pulse circuit electrically coupled to the plurality of electrodes, the pulse circuit comprising a single output capacitor and a voltage regulator, the pulse circuit configured to:
        charge the single output capacitor of the pulse circuit to an initial charge level that is at least sufficient to deliver a pacing pulse having the second amplitude of backup pacing pulses;
        use the voltage regulator to deliver a test pacing pulse having the first amplitude to the plurality of electrodes by only partially discharging the single output capacitor of the pulse circuit after the single output capacitor of the pulse circuit has been charged to the initial charge level that is at least sufficient to deliver a pacing pulse having the second amplitude of backup pacing pulses; and
        subsequently deliver a backup pacing pulse having the second amplitude, that is greater than the first amplitude, to the plurality of electrodes by further discharging the single output capacitor of the pulse circuit after the test pacing pulse having the first amplitude has been delivered.

2. The leadless pacemaker of claim 1, wherein the pulse circuit is configured to recharge the single output capacitor of the pulse circuit to the initial charge level that is at least sufficient to deliver a pacing pulse having the second amplitude, between delivery of the test pacing pulse and delivery of the backup pacing pulse, by recharging the single output capacitor of the pulse circuit by less than or approximately the charge delivered by the test pacing pulse.

3. The leadless pacemaker of claim 1, wherein:
    the initial charge level is at least sufficient to enable both the test pacing pulse and the backup pacing pulse to be delivered sequentially without the single output capacitor of the pulse circuit being recharged between delivery of the test pacing pulse and delivery of the backup pacing pulse; and
    the pulse circuit is configured to deliver both the test pacing pulse and the backup pacing pulse sequentially without recharging the single output capacitor of the pulse circuit between delivery of the test pacing pulse and delivery of the backup pacing pulse.

4. The leadless pacemaker of claim 1, wherein the regulator of the pulse circuit comprises a low-dropout (LDO) linear regulator configured to regulate discharging of the single output capacitor of the pulse circuit to thereby deliver the test pacing pulse.

5. The leadless pacemaker of claim 1, wherein the pulse circuit further comprises a digital to analog converter configured to set the first amplitude of the test pacing pulse by setting a programmable reference of the regulator.

6. The leadless pacemaker of claim 1, wherein the pulse circuit further comprises a plurality of switches that are controlled to selectively discharge the single output capacitor of the pulse circuit to deliver the test and backup pacing pulses.

7. The leadless pacemaker of claim 1, wherein the pulse circuit is configured to deliver the backup pacing pulse between approximately 50 milliseconds (ms) and 250 ms after the test pacing pulse.

8. A pulse circuit for use in a cardiac stimulation device used for selectively delivering test pacing pulses having a first amplitude and backup pacing pulses having a second amplitude that is greater than the first amplitude, the pulse circuit configured to electrically couple to a plurality of electrodes and comprising:
    a single output capacitor; and
    charge and discharge circuitry electrically coupled to the single output capacitor of the pulse circuit and configured to:
        charge the single output capacitor of the pulse circuit to an initial charge level that is at least sufficient to deliver a pacing pulse having the second amplitude of backup pacing pulses;
        after the single output capacitor of the pulse circuit is charged to the initial charge level that is at least sufficient to deliver a pacing pulse having the second amplitude of backup pacing pulses, only partially discharge the single output capacitor of the pulse circuit to deliver a test pacing pulse having the first amplitude to the plurality of electrodes; and after the test pacing pulse having the first amplitude is delivered, further discharge the single output capacitor of the pulse circuit to deliver a backup pacing pulse having the second amplitude to the plurality of electrodes.

9. The pulse circuit of claim 8, wherein the charge and discharge circuitry is further configured to recharge the single output capacitor of the pulse circuit, to the initial charge level that is at least sufficient to deliver a pacing pulse having the second amplitude, between delivery of the test pacing pulse and delivery of the backup pacing pulse.

10. The pulse circuit of claim 8, wherein:
the initial charge level is at least sufficient to enable both a test pacing pulse and a backup pacing pulse to be delivered sequentially without the single output capacitor of the pulse circuit being recharged between delivery of the test pacing pulse and delivery of the backup pacing pulse; and the charge and discharge circuitry is further configured to deliver the test pacing pulse and the backup pacing pulse sequentially without recharging the single output capacitor of the pulse circuit between delivery of the test pacing pulse and delivery of the backup pacing pulse.

11. The pulse circuit of claim 8, wherein the charge and discharge circuitry further comprises a regulator configured to regulate discharging of the single output capacitor of the pulse circuit to thereby deliver the test pacing pulse.

12. The pulse circuit of claim 11, wherein the charge and discharge circuitry further comprises a digital to analog converter configured to set the first amplitude of the test pacing pulse by setting a programmable reference of the regulator.

13. The pulse circuit of claim 8, wherein the charge and discharge circuitry further comprises a plurality of switches that are controlled to selectively discharge the single output capacitor of the pulse circuit to deliver the test and backup pacing pulses.

14. The pulse circuit of claim 8, wherein the charge and discharge circuitry is configured to deliver both the test and backup pacing pulses within a single output cardiac cycle.

15. A method for use by a cardiac stimulation device having a pulse circuit including a single output capacitor, the method used for selectively delivering test pacing pulses having a first amplitude and backup pacing pulses having a second amplitude that is greater than the first amplitude, the method comprising:

charging the single output capacitor of the pulse circuit to an initial charge level that is at least sufficient to deliver a pacing pulse having the second amplitude of backup pacing pulses;

after the single output capacitor of the pulse circuit has been charged to the initial charge level that is at least sufficient to deliver a pacing pulse having the second amplitude of backup pacing pulses, only partially discharging the single output capacitor of the pulse circuit to deliver a test pacing pulse having the first amplitude to a plurality of electrodes coupled to the single output capacitor of the pulse circuit; and after delivering the test pacing pulse having the first amplitude, further discharging the single output capacitor of the pulse circuit to deliver a backup pacing pulse having the second amplitude to the plurality of electrodes.

16. The method of claim 15, further comprising recharging the single output capacitor of the pulse circuit to the initial charge level that is at least sufficient to deliver a pacing pulse having the second amplitude, between delivery of the test pacing pulse and delivery of the backup pacing pulse, by recharging by less than or approximately the charge delivered by the test pacing pulse.

17. The method of claim 15, wherein partially discharging the single output capacitor of the pulse circuit comprises regulating discharging of the single output capacitor of the pulse circuit using a regulator to thereby deliver the test pacing pulse.

18. The method of claim 15, further comprising setting the first amplitude of the the test pacing pulse using a digital to analog converter.

19. The method of claim 15, wherein the single output capacitor of the pulse circuit is not recharged between delivery of the test pacing pulse and delivery of the backup pacing pulse.

20. The method of claim 15, further comprising using a plurality of switches to selectively discharge the single output capacitor of the pulse circuit to deliver the test and backup pacing pulses.

\* \* \* \* \*